(12) United States Patent
Neuberger et al.

(10) Patent No.: US 6,808,901 B1
(45) Date of Patent: Oct. 26, 2004

(54) PRODUCTION OF CHIMERIC ANTIBODIES

(75) Inventors: Michael Samuel Neuberger, Cambridge (GB); Terence Howard Rabbitts, Hildersham (GB)

(73) Assignee: Celltech R&D Limited, Slough (GB)

( * ) Notice: Subject to any disclaimer, the term of this patent is extended or adjusted under 35 U.S.C. 154(b) by 1826 days.

(21) Appl. No.: 08/469,786

(22) Filed: Jun. 6, 1995

Related U.S. Application Data

(63) Continuation of application No. 08/185,440, filed on Jan. 24, 1994, now abandoned, which is a continuation of application No. 07/994,078, filed on Dec. 17, 1992, now abandoned, which is a continuation of application No. 07/489,207, filed on Mar. 6, 1990, now abandoned, which is a division of application No. 06/865,816, filed on May 2, 1986, now abandoned, which is a continuation of application No. PCT/GB85/00392, filed on Sep. 3, 1985.

(30) Foreign Application Priority Data

Sep. 3, 1984 (GB) .............................................. 8422238

(51) Int. Cl.$^7$ .............................................. C12N 15/00
(52) U.S. Cl. ................. 435/69.7; 530/387.3; 530/387.1
(58) Field of Search .......................... 530/387.3, 387.1, 530/388.1, 387, 388; 435/69.6, 69.7, 70.21, 172.3, 69.1, 15, 11, 47, 51, 111

(56) References Cited

U.S. PATENT DOCUMENTS

| | | | | |
|---|---|---|---|---|
| 4,340,535 A | * | 7/1982 | Voisin et al. | |
| 4,703,004 A | * | 10/1987 | Hopp et al. | ................... 435/68 |
| 4,816,567 A | * | 3/1989 | Cabilly et al. | ............... 530/387 |
| 5,169,939 A | | 12/1992 | Gefter et al. | ............ 530/387.3 |

FOREIGN PATENT DOCUMENTS

EP 0120694 * 3/1984

OTHER PUBLICATIONS

Cruse et al Illustrated Dictionary of Immunology, CRC Press, p. 107, 1995*
*Biochemistry*, by A.L. Lehninger, Published by World Publishers, Inc., New York, in 1970, pp. 28 and 125.*
Neuberger, EMBO Journal 2(8) :1373–1378 (1983).*
Oi et al., Proc. Natl. Acad. Sci. 80 :825–829 (1983).*
Zoller et al, DNA 3:479 (1984).
Dictionary of Genetics and Cell Biology 1987 p. 212.
Iida et al, EMBO 1:755 (1982).
Genetic Engineering vol. 6, Chapter by Weinstock pp. 31–48 (1984).

* cited by examiner

*Primary Examiner*—Larry R. Helms
(74) *Attorney, Agent, or Firm*—Woodcock Washburn LLP

(57) ABSTRACT

A process for the production of a chimeric antibody, comprising: a) preparing a replicable expression vector including a suitable promoter operably linked to a DNA sequence comprising a first part which encodes at least the variable region of the heavy or light chain of an Ig molecule and a second part which encodes at least part of a second protein; b) if necessary, preparing a replicable expression vector incuding a suitable promoter operably linked to a DNA sequence which encodes at least the variable region of a complementary light or heavy chain respectively of an Ig molecule; c) transforming an immortalized mammalian cell line with the or both prepared vectors; and d) culturing said transformed cell line to produce the chimeric antibody; chimeric antibodies produced by this process; and plasmids and transformed cell lines used in the process.

11 Claims, 10 Drawing Sheets

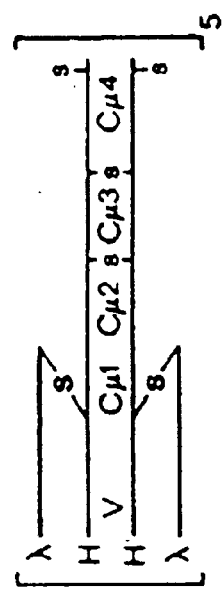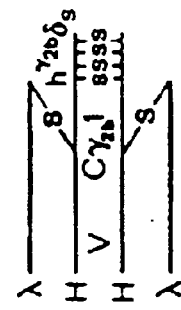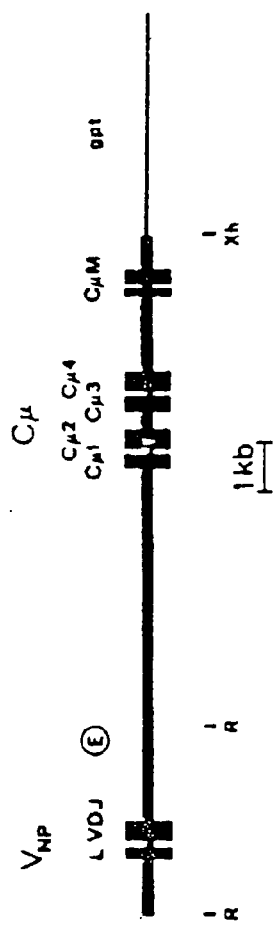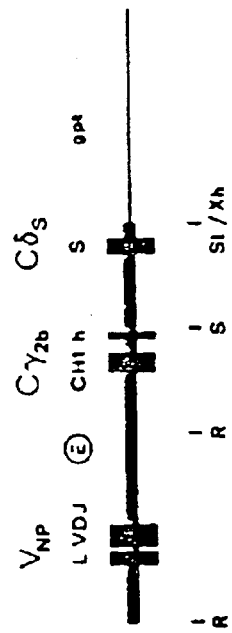
FIG. 1B
FIG. 3B
FIG. 1A
FIG. 3A

FIG. 9
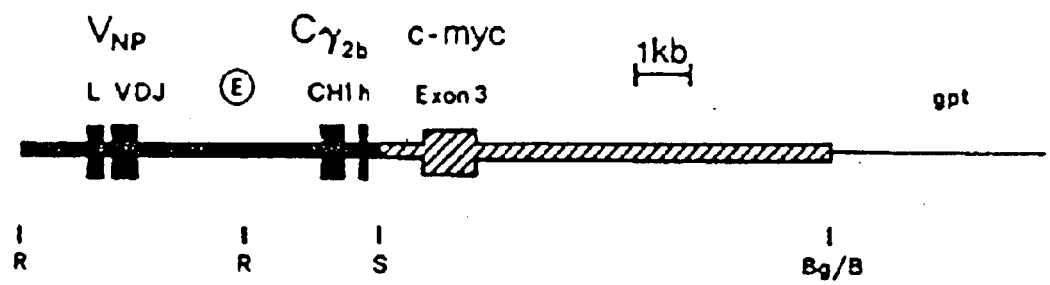
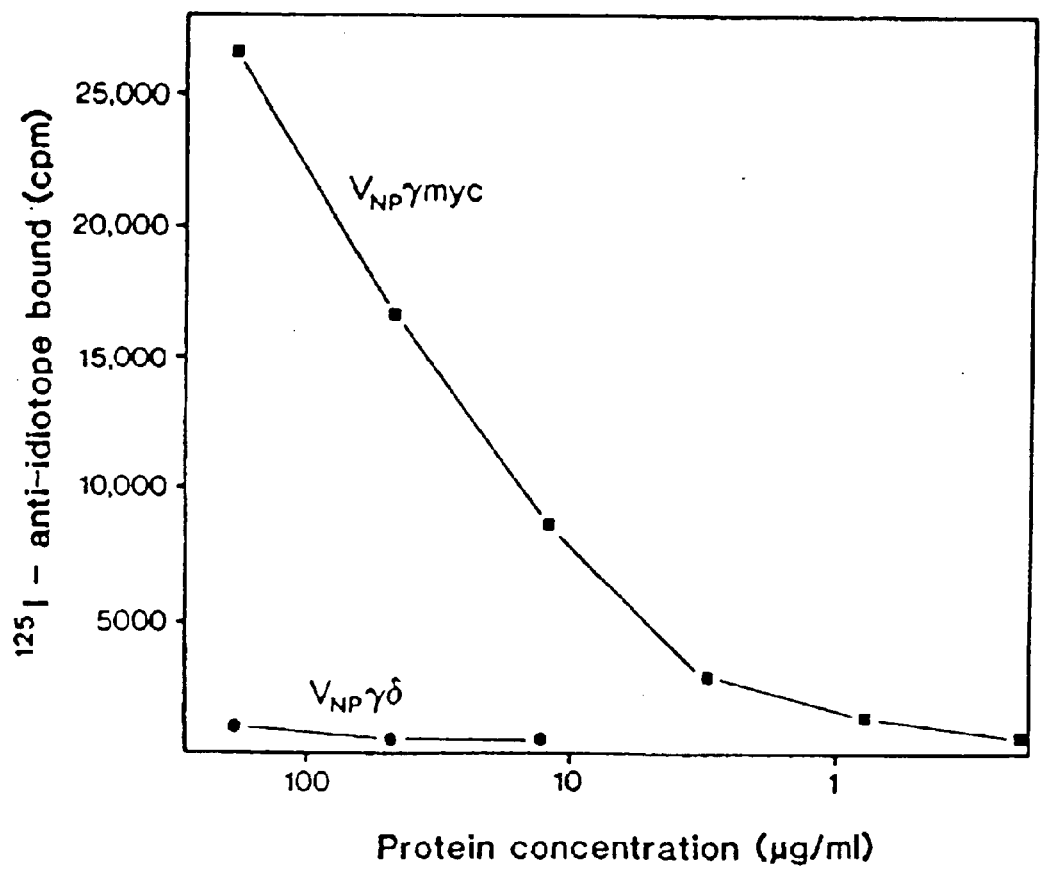
FIG. 10

FIG. 11 pSV - V$_{NP}$Hε mouse | human
|Enh|←—V$_{NP}$—|←——Cε——→|

LVDJ  Cε1 Cε2 Cε3 Cε4    gpt    amp

R R    B         B              R

|—1kb—| a.
Markers | JW8/5/13

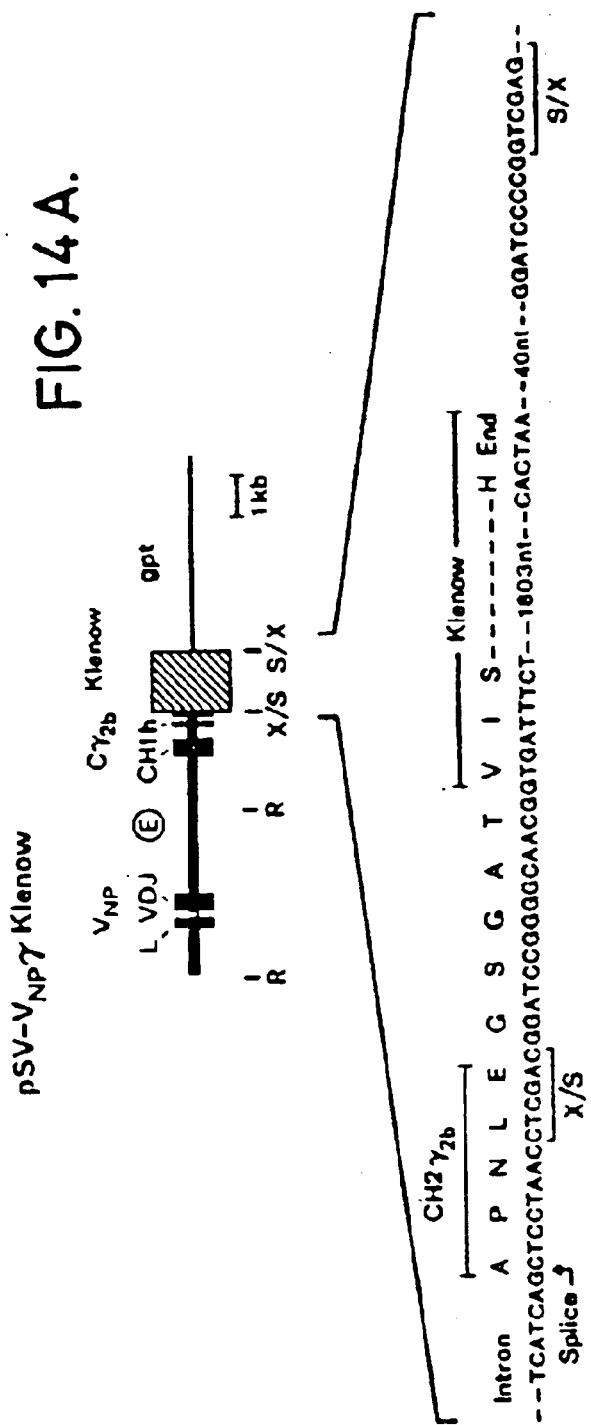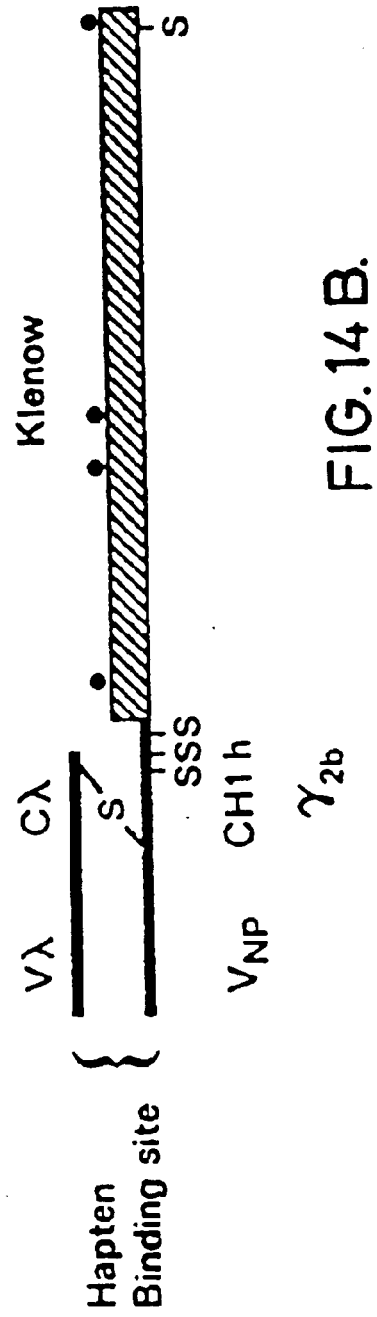
FIG. 14A.
FIG. 14B.

PRODUCTION OF CHIMERIC ANTIBODIES

This is a continuation of application Ser. No. 08/185,440, filed on Jan. 24, 1994, now abandoned, which is a continuation of Ser. No. 07/994,078, filed Dec. 17, 1992, now abandoned, which is a continuation of Ser. No. 07/489,207, filed Mar. 6, 1990, now abandoned, which is a divisional of Ser. No. 06/865,816, filed May 2, 1986 now abandoned. This application is a continuation of PCT/GB85/00392 filed Sep. 3, 1985.

The present invention relates to a process for the production of chimeric antibodies using recombinant DNA techniques.

In the present application, the term chimeric antibody is used to describe a protein comprising at least the antigen binding portion of an immunoglobulin molecule (Ig) attached by peptile linkage to at least part of another protein.

In recent years, advances in molecular biology based on recombinant DNA techniques have provided processes for the production of a wide range of heterologous polypeptides by transformation of host cells with heterologous DNA sequences vhich code for the production of the desired products.

EP-A-O 088 994 (Schering Corporation) proposed the construction of recombinant DNA vectors comprising a ds DNA sequence vhich codes for a variable region of a light or a heavy chain of an Ig specific for a predetermined ligand. The ds DNA sequence is provided with initiation and termination codons at its 5'- and 3'-termini respectively, but lacks any nucleotides coding for amino acids superfluous to the variable region. The ds DNA sequence is used to transform bacterial cells. The application does not contemplate the production of chimeric antibodies.

EP-A-1 102 634 (Takeda Chemical Industries Limited) describes the cloning and expression in bacterial host organisms of genes coding for the whole or a part of human IqE heavy chain polypeptide, but does not contemplate the production of chimeric antibodies.

EP-A-0 125 023 (Genentech Inc. et al.), which was published after the priority date of the present application, proposes the use of recombinant DNA techniques in bacterial cells to produce Ig's which are analogous to those normally found in vertebrate systems and to take advantage of the gene modification techniques proposed therein to construct chimeric Ig's or other modified form of Ig.

It is believed that the proposals set out in the above Genentech application did not lead to the expression of any significant quantities of Ig polypeptide chains, nor to thes production of Ig activity, nor to the secretion and assembly of the chains into the desired chiaeric Ig's.

The production of monoclonal antibodies was first disclosed by Kohler and Milstein (Kohler, G. and Milstein, C., Nature, 256, 495–497, 1975). Such monoclonal antibodies have found widespread used not only as diagnostic reagents (see, for example, 'Immunology for the 80s, Eds. Voller, A., Bartlett, A., and Bidwell, D., MTP Press, Lancaster, 1981) but also in therapy (see, for example, Ritz, J. and Schlossman, S. F., Blood, 59, 1–11, 1982).

The recent emergence of techniques allowing the stable introduction of Ig gene DNA into myeloma cells (see, for example, Oi, V. T., Morrison, S. L., Herzenberg, L. A. and Berg, P., PNAS USA, 80, 825–829, 1983; Neuberger, M. S., EMBO J., 2, 1373–1378, 1983; and Ochi, T., Hawley, R. G., Hawley, T., Schulman, M. J., Traunecker, A., Kohler, G. and Hozumi, N., PNAS USA, 80, 6351–6355, 1983), has opened up the possibility of using in vitro mutagenesis and DNA transfection to construct recombinant Ig's possessing novel properties.

However, it is known that the function of an Ig molecule is dependent on its three dimensional structure, which in turn is dependent on its primary amino acid sequence. Thus, changing the amino acid sequence of an Ig may adversely affect its activity. Moreover, a change in the DNA sequence coding for the Ig may affect the ability of the cell containing the DNA sequence to express, secrete or assemble the Ig.

It is therefore, not at all clear that it will be possible to produce functional altered antibodies by recombinant DNA techniques.

Simiar considerations apply to other proteins. It therefore cannot be expected that fusion of a gene coding for at least part of an Ig with a gene coding for at least part of another protein will lead expression of any protein, let alone expression of protein which can be secreted and assembled to give a functional chineric antibody.

However, the present inventors have now discovered unexpectedly that it is possible to produceby recombinant DNA techniques secreted, assembled chimeric antibodies in which both parts of the protein are functional.

This surprising result is achieved by the use of the process of the present invention, which comprises:

a) preparing a replicable expression vector including a suitable promoter operably linked to a DNA sequence comprising a first part which encodes at least the variable region of the heavy or light chain of an Ig molecule and a second part which encodes at least part of a second protein;

b) if necessary, preparing a replicable expression vector including a suitable promoter operably linked to a DNA sequence which encodes at least the variable region of a complementary light or heavy chain respectively of an Ig molecule;

c) transforming an imortalised mammalian cell line with the or both prepared vectors; and d) culturing said transformed cell line to produce a chimeric antibody.

The immortalised cell line is preferably of lymphold origin, such as a myeloma, hybridoma, trioma or quadroma cell line. The cell line may also comprise a normal lymphoid cell, such as a B-cell, which has been inmortalised by transformation with a virus, such as the Epstein-Barr virus. Most preferably, the immortalised cell line is a myeloma cell line or a derivative thereof.

It is known that some immortallsed lymphoid cell lines, such as ayeloma cell lines, in their normal state secrete isolated Ig light or heavy chains. If such a cell line is transformed with the vector prepared in step a) of the process of the invention, it will not be necessary to carry out step b) of the process, provided that the normally secreted chain is complementary to the part of the Ig molecule encoded by the first part of the vector prepared in step a).

However, where the immortalised cell line does not secrete or does not secrete a complementary chain, it will be necessary to carry out step b). This step may be carried out by further manipulating the vector produced in step a) so that this vector encodes not only the fusion of variable region and second protein, but also the complementary variable region. However, preferably step b) is carried out by preparing a second vector which is used to transform the immortalised cell line.

The techniques by which such vectors can be produced and used to transform the immortalised cell lines are well known in the art, and do not form any part of the invention. However, they are well illustrated in the following Examples.

In the case where the immortalised cell line secretes a complementary light or heavy chain, the transformed cell line may be produced by transforming a suitable bacterial cell with the vector and then fusing the bacterial cell with the immortalised cell line, e.g. by Spheroplast fusion.

The first part of the DNA sequence say be joined directly to the second part thereof. Alternatively, the first part may be joined to the second part by an intervening sequence which encodes a specific cleavage sequence, for instance a Factor Xa cleavage sequence as described in our copending European patent application No. 85303414.8. Reference may be made to this application for further discussion of the use to specific cleavage sequences.

The second part of the DNA sequence may encode:

i) at least part, for instance the constant region of a heavy chain, of an Ig molecule of different species, class or subclass;

ii) at least the active portion or all of an enzyme;

iii) a protein having a known binding specificity;

iv) a protein expressed by a known gene but whose sequence, function or antigenicity is not known; or v) a protein toxin, such as ricin.

The chimeric antibody produced in case i) above will be of use in a number of applications. For instance, an established cell line may produce an Ig molecule having a useful specificity. However it may be of a class which is diagnostically or therapeutically undesirable, or it may not be secreted in useful quantities. For instance, Ig of glass M is known to be difficult to use in rapid immunoassay techniques and is generally inconvenient for use in therapy, whereas Ig of class G can be readily used in these techniques. Therefore, it would be possible to produce a useful immunoassay reagent or therapeutic agent by replacing the IgM heavy chain constant region with an IgG heavy chain constant reglon. A particular example of such use would be in the production of a chimeric antibody having an anti Rh specificity, derived from an IgM secreting myeloma and IgG reactivity provided by an IgG derived heavy chain constant region.

Alternatively, the chimeric antibody could comprise an IgG derived variable region and an Ig E derived heavy chain constant region. Such a chimeric antibody could be used to investigate the action of IgE on mast cells, in diagnostic assays, for instance calibrating test procedures or, in therapy, to inhibit allergic reactions caused by the action of normal IgE molecules on mast cells.

In another alternative, the chimeric antibody may be used to alter the complement binding activity of an antibody, again by changing the heavy chain constant region.

In a further alternative, the chimeric antibody may be constructed to resemble an (Fab')$_2$ fragment of a normal antibody.

The chimeric antibody produced in case ii) above may be used, in particular, in an enzyme linked immunoassay (ELISA) system, in place of the present use of separate antibodies and enzymes.

The chimeric antibody produced in case iii) above may also be used in immunoassays. For instance, the protein may have a binding specificity for an easily detectable label, such as a heavy or radioactive metal or a dyed or dyeable molecule. For instance, it would be possible to produce a divalent chimeric antibody having a different variable region at each end, the ends being connected by at least a part of a constant region.

The chimeric antibody produced in case iv) above may be used to investigate the products of known genes. For instance, it may be known that a particular gene produces a protein involved in the surface marking of a cell. However, the exact nature of the surface marker may not be known. The chimeric antibody produced in case iv) will comprise the protein product of the gene, which can therefore be more readily characterised. Moreover, antibodies to this gene product could be raised and used to investigate with certainty the distribution of the gene product on a cell surface.

The chimeric antibody produced in case v) above will clearly be of use in therapy, for instance as a targetted cytotoxic agent for cancer therapy. In this respect reference may be made to an article by Thorpe et al. (Thorpe, P. E., Edwards, D. C., Davies; A. J. S. and Ross, W. C. J., in 'Monoclonal Antibodies in Clinical Medicine', 167–201, Eds., McMichaele A. J. and Fabre, J. W., Academic Press, 1982).

The chimeric antibodies produced by the present process, especially where the DNA sequence encodes a specific cleavage site, may be used for purifying the second protein. For instance, the variable region may be made specific for a hapten whicn can be immobilised on a chromatography medium. The chimeric antibody can then be immobilised by affinity chromatography and contaminating material can be washed away. The second protein can then be cleaved from the variable region either before or after the variable region is eluted from the chromatography medium.

The chimeric proteins of the type referred to in cases ii) to iv) above and in the preceding paragraph also comprise aspects of the present invention.

The present invention is described in more detail, by way of non-limiting illustration only, with reference to the accompanying drawings; in which:

FIG. 1A shows the structure of plasmid pSV-Vul;

FIG. 1B shows the predicted structure of the IgM molecule produced by the J558L cell line transformed with the plasmid pSV-Vul;

FIG. 3A shows the structure to plasmid pSV-V$_{NP}$ γδ;

FIG. 3B shows the predicted structure of the F(ab)'$_2$ chimeric antibody prcduced by the J558L cell line transformed with the plasmid pSV-V$_{NP}$ γδ;

FIG. 9 shows the structure of plasmid pSV-V$_{NP}$ γ myc;

FIG. 10 shows an assay for c-myc antigenic determinant in Fab-myc;

FIG. 11 shows the structure of plasmid pSV-V$_{NP}$ H;

FIG. 13 shows polyacrylamide gels of purified chimeric IgE;

FIG. 14A shows the structure of plasmid pSV-V$_{NP}$ γ Klenow;

FIG. 14B shows the predicted structure of the Fab-γ Klenow chimeric antibody produced by the J558L cell line transformed with plasmid pSV-V$_{NP}$ γ-Klenow;

Figure 4:
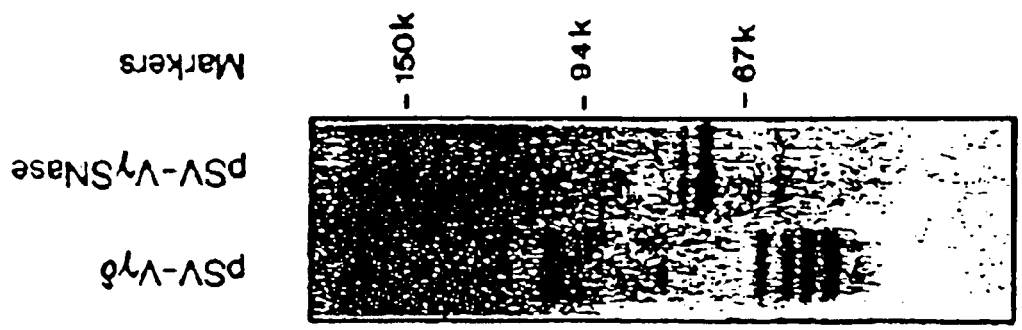
FIG. 4 shows polyacrylamide gels of purified products produced by the J558L cell line transformed with various plasmids.

In the drawings which show plasmids, thin horizontal lines depict pSV2 gpt vector, thick lines represent mouse or human Ig gene DNA, exons are represented by boxes, and hatched areas represent second (non-Ig) protein DNA.

The locations of the heavy chain locus transcription enhancer element (E) and the qpt gene are indicated. Restriction endonuclease cleavage sites are abbreviated as follows: R=Eco RI; Xh=Xho I; S=Sac I; and Sl/Xh=a sequence formed by joining a Sal I site to an Xho I site. The sequence in presented around the Xho I site of plasmld PSV-V$_{NP}$ γ SNase, which forms a junction of the γ2b CH2 exon and the SNase gene.

In the diagrammatic representations of the predicted structures of Ig molecules and chimeric antibodies, disulphide linkages between heavy (H) and light (λ) chains are indicated by (—S—). Only one subunit of the decavalent pSV-Vul encoded IgM is illustrated.

In the following Examples use is made of an established mouse plasmacytona cell line J558L which secretes λ$_1$ light chains but does not produce any Ig heavy chain. This plassacytoma cell line is described by Oi et al. (Oi, V. T., Morrison, S. L., Herzenberg, L. A., and Berg, P., PNAS USA, 80, 825–829,1983).

In the Examples, reduced samples were analysed on 12% polyacrylamide gels, while unreduced samples were analysed on 7% polyacrylamide gels.

The Examples also use plasmaid pSV-Vμl described by Neuberger, M. S., EMBO J., 2, 1373–1378, 1983. This plasmid comprises a complete mouse immuoglobin μ gene cloned into the expression vector pSV2 gpt, and is shown in FIG. 1A. The Ig μ polypeptide encoded by this plasmid has a heavy chain variable region, V$_H$, characteristic of λ$_1$ light chain-bearing mouse antibodies which are specific for the hapten 4-hydroxy-3-nitrophenacetyl (NP): NP binding activity should therefore be formed following association of the pSV-Vμl encoded heavy chain with mouse λ$_1$ light chains.

To confirm this, pSV-Vμl DNA was introduced by spheroplast fusion into the J558L cell line and growth in selective medium essentially as described in the Neuberger article referred to above, except that HAT was omitted from the selective medium and mycophenolic acid was used at 5 μg/ml, as described in the Oi et al. article referred to above. Cells were cloned by limiting dilution. Antibody samples were purified from supernatants of cloned J558L transfectants grown in Dulbecco's modified Eagle's medium containing 5% foetal calf serum. Supernatants (2 liters) were passed over 2 ml columns of 4-hydroxy-5-iodo-3-nitrophenacetyl-amino-caproic acid Sepharose (NIPcap-Sepharose) and antibody eluted from the washed sorbent with 1 mH NIPcapOH in phosphate buffered saline. Bioaynthetically labelled antibody was purified an 40 μl NIPcap-Sepharose columns from supernatants of cells incubated for 4 h at 37° C. in medium containing L-[$^{35}$S]-methionine. Tunicamycin was, if required, included during the labelling and during a 2 h preincubatlon at 8 μg/ml (parallel incubations with an IgE secreting cell line confirmed the efficacy of this treatment).

Figure 2:
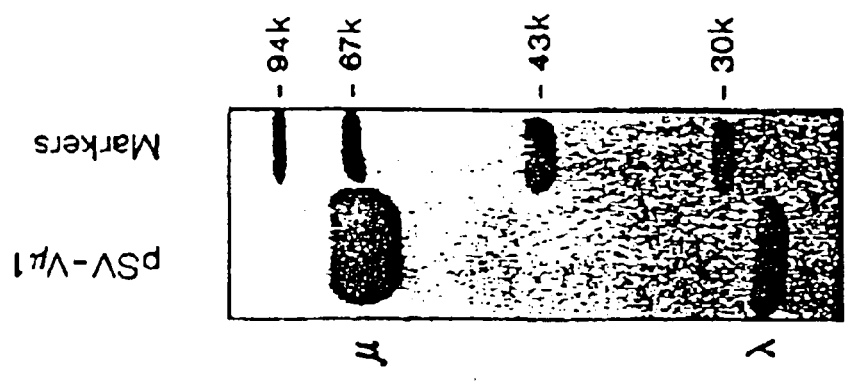
FIG. 2 shows polyacrylamide gels of the purified IqM molecule produced by the J558L cell line transformed with the plasmid pSV-Vul.

Stably transfected cells were selected and cloned by limiting dilution. Twenty clones were analysed by radioimmunoassay and each secreted high levels of an NP-specific IgM antibody. As illustrated in FIG. 2, homogeneous anti-NP IgM antibody can te purified from supernatants of pSV-Vμl transfected clones with a yield of about 3 mg/ml.

In FIG. 2: lane (a) shows purified antibody (30 μg) which has been boiled with 2-mercaptoethanol prior to electrophoresis and stained with coomassie blue; and lane (b) shows markers to enable the molecular weight of the chains to be estimated. The predicted structure of the Ig molecule isolated from pV-Vμl transfected clones is shown in FIG. 1B.

EXAMPLE 1

(Fab)'$_2$—like Chimeric Antibody

A derivative of pSV-Vμl was constructed in which the Cμ exons were replaced by the CH1 and hinge exons of the mouse γ2b gene. To provide translation termination and polyadenylation sequences, an exon, Cδs, derived from the gene encoding secreted mouse δ chains was placed at the 3' end of the gene. The constructed plasmid pSV-V$_{NP}$ γδ is shown in FIG. 3A.

To construct plasmid pSV-V$_{NP}$ γδ, the V$_{NP}$ exons from pSV-Vμl contained on a common Eco RI fragment are placed in a vector consisting of the Bam HI-Eco RI fragment of pSV2gpt (see Mulligan, R. C. and Berg, P., PNAS USA, 78, 2072–2076, 1981) with an Xho I adapter in the Bam HI site. The plasmid contains an Eco RI-Sac I mouse Cγ2b fragcent derived from phage λ MYG9 (see Neuberger, M. S. and Calabi, P., Nature, 305, 240–243, 1983). The mouse Cδ$_s$ exon as the PSV-V$_{NP}$ γδ plasmld is contained in a Bam HI fragment of phage Ch 257 3 (see Cheng, H.-L., Blattner, F. R., Fitzmaurice, L., Mushinski, J. F., and Tucker, P. W., Nature, 296, 410–415, 1982) which was obtained as a Sac I-Sal I fragment after cloning in M13mp 11.

The truncated heavy chain gene of pladid pSV-V$_{NP}$ γδ would be expected to direct the synthesis of a F(ab)'$_2$—like chimeric antibody, as shown diagrammatically in FIG. 3B, conaisting of two IgG2b Fab molecules disulphide linked together through the γ2b hinge with a 21 amino acid tail piece at the carboxy terminus encoded by the Cδ$_s$ exon.

Figure 5:
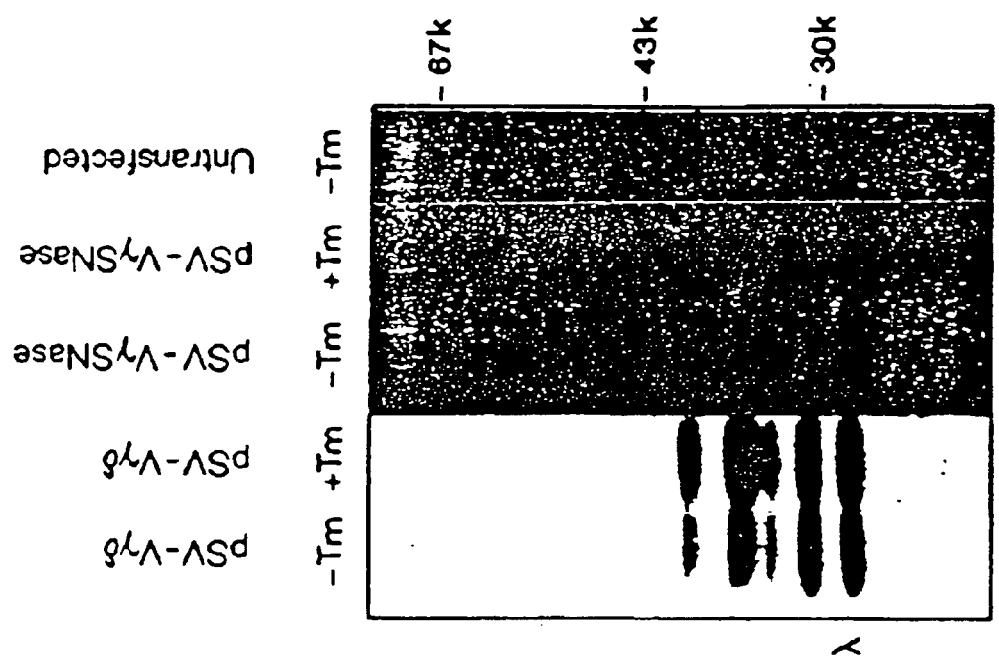
FIG. 5 shows polyacrylamide gels of purified products produced by the J558L cell line transformed with various plasmids in the presence or absence of tunicamycin.

Plasmid pSV-V$_{NP}$ γδ was transfected into J558L cells and radioimmunoassay revealed that stably transfected cells secreted high levels of λ$_1$-bearing anti-NP antibody. This NP-specific antibody was purified from culture supernatants of several transfected clones with a yield of 5 to 10 mg/l. Polyacrylamide gel electrophoresls of the purified material (FIG. 4) shows that the major protein species has an unreduced molecular weight of about 110,000 daltons. After reduction, a band comigrating with λ light chain as well as several higher molecular weight polypeptides are observed. The most abundant of these larger polypeptides has a molecular weight of 31,000 and would constitute the heavy chain of the F(ab)'$_2$ like antibody. However, there is clear contamination of the pSV-V$_{NP}$ γδ F(ab)'$_2$ antibody with other NP-binding material that has an unreduced molecular weight of around 50,000 daltons and is composed of λ$_1$ light chains and one of several heavy chains in the molecular weight range 36,000 to 40,000. The presence of this minor antibody component does not reflect glycosylation heterogeneity as the electrophoretic nobility of the pSV-V$_{NP}$ γδ encoded anti-NP antibody is unaffected by inclusion of tunicamycin in the incubation medium during biosynthetic labelling experiments (FIG. 5). It is likely that the minor bands differ from the F(ab)'$_2$ antibody in the carboxy terminal portion of the heavy chain, possibly as a result of alternative processing of pSV-V$_{NP}$ γδ immunoglobulin gene RNA transcripts. Nevertheless, despite the contaminating bands, it is clear that F(ab)'$_2$-like antl-NP antibody can be synthesized and secreted in good yield by pSV-V$_{NP}$ γδ transfected J558L cells.

EXAMPLE 2

Fab-nuclease Chimeric Antibody

Figure 6B:
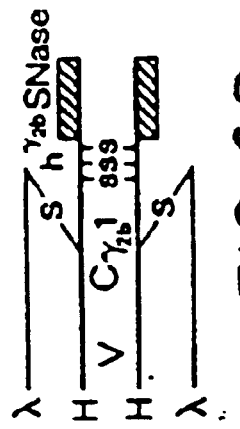
FIG. 6B shows the predicted structure of the chimeric antibody produced by the J558L cell line transformed with the plasmid pSV-V$_{NP}$ γ SNase.
Figure 6A:
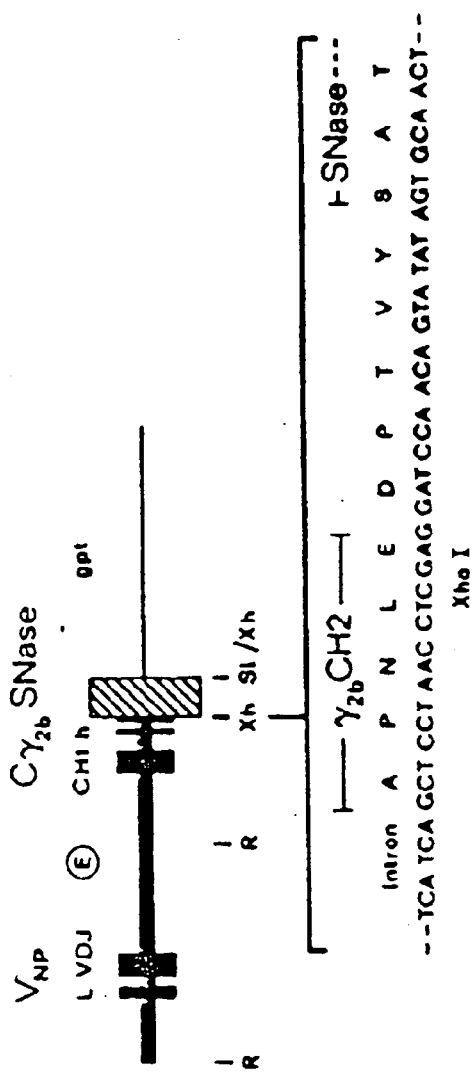
FIG. 6A shows the structure of plasmid pSV-V$_{NP}$ γ SNase.

A DNA restriction fragment containing the S. aureus nuclease (SNase) genei was inserted into the Xho I site located in the CH2 exon of the mouse γ2b gene. Plasmid pSV-V$_{NP}$ SNase was asseabled by inserting the V$_{NP}$ exons contained on the common Eco RI fragment into the vector comprising the Bam HI-Eco RI fragment of pSV2gpt with an Xho I adapter in the Bam HI site as described in Example 1. An Eco RI-Xho I mouse Cγ2b fragment derived from phage λMYG9 was also inserted in the vector, so that pSV-V$_{NP}$ γSNase contains the γ2b CH1, hinge and 5' end of the CH2 exons. The SNase coding region is derived from an M13mp8 clone containing an S. aureus Sau 3A fragment in the Bam HI site. Removal of the SNase gene from M13mp8 as a Bam-Sal I fragment and recloning in M13mp12W (see Karn, J., Mathes, H. W. D., Gait, M. J., and Brenner, S., Gene, 32, 217–224, 1984) allowed its isolation as an Xho I-Sal I fragment for final assembly of the pSV-V$_{NP}$ SNase, the structure of which is shown in FIG. 6A.

The heavy chain gene of pSV-V$_{NP}$ γSNase is similar to that of pSV-V$_{NP}$ γδ except that the Cδ$_s$ exon has been removed and replaced by an exon containing the first four codons of the γ2b CH2 exon fused in phase to the nuclease coding region. SV40-derived sequences of the pSV2gpt-derived vector provide polyadenylation signals.

J558L cells were transfected with pSV-V$_{NP}$ γ SNase and cells surviving in selective medium were cloned by limiting dilution. Radioimmunoassay of supernatants of cloned transfectants revealed that about one third were positive for the production of λ-bearing anti-NP antibody. Positive clones yielded between 1 mg/l and 10 mg/l of NP binding antibody, which has the predicted structure shown in FIG. 6B.

Analysis of biosynthetically labelled antibody by gel electrophoresis reveals a band comigrating with λ$_1$ light chain as well as two heavy chain bands of molecular weight 45,000 and 46,000 (FIG. 5). The difference between these two heavy chains has not been identified but their mobilities agree well with the predicted mobility of the V$_{NP}$ γ SNase heavy chain. Although the sequence Asn-Asn-Thr is present in SNase, the two V$_{NP}$ γ SNase heavy chain bands are still present in samples purified from supernatants of cells that have been biosynthetically labelled in the presence of tunicamycin (FIG. 5). This demonstrates that the difference between the two pSV-V$_{NP}$ γ SNase heavy chains is not due to N-linked glycosylation. The V$_{NP}$ γ SNase antibody appears somewhat more heterogenous on a non-reduced gel, giving bands with the expected mobilities of both the F(ab)'$_2$-SNase and Fab-SNase (FIG. 4). The presence of SNase on the heavy chain carboxy terminus might inhibit disulphide linking of the γ2b hinge regions.

To test for nuclease activity in the V$_{NP}$ γ SNase preparation, samples which had been purified on hapten-Sepharose columns were incubated wlth single stranded DNA substrate. Digestion of the DNA was monitored following agarose gel electrophoresis as follows. Single steranded M13DNA (2 μg) was incubated at 37° C. for 30 minutes in 25 mM sodium borate, 250 mM NaCl, 10 cm CaCl$_2$, PH 8.5 (20 μl) containing varying amounts of V$_{NP}$ γ SNase chimeric antibody or of purified S. aureus nuclease. The quantities of antibody/enzyme used are given in nanograms. DNA in the samples was then analysed by ethidium bromide fluorescence after electrophoresis through a 1.2% agarose gel. A Hind III digest of phage DNA provides size markers. Ca$^{++}$ dependency of the nuclease activity was confirmed by ruing incubations in the presence of 40 mM MgCl$_2$, 25 mM EGTA.

Figure 7:
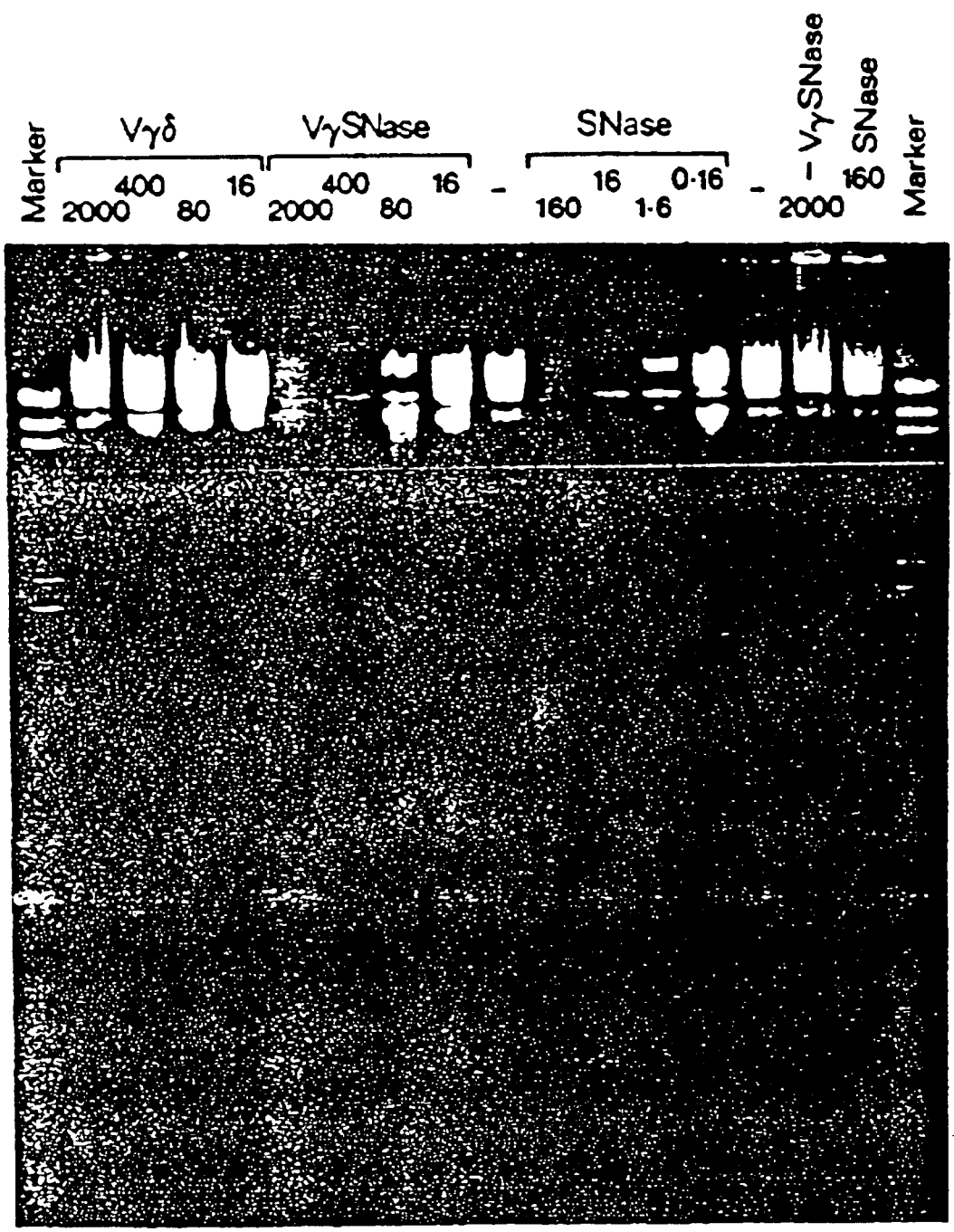
FIG. 7 shows polyacrylamide gels used for monitoring SNase activity.

As shown in FIG. 7, V$_{NP}$ γ SNase but not V$_{NP}$ γδ antibodies show nuclease activity and this activity—like that of authentic S. aureus nuclease—is dependent on Ca$^{++}$ but not Mg$^{++}$ ions. As judged on a molar basis, the catalytic activity of the V$_{NP}$ γ SNase sample is about 10% that of authentic S.aureus nuclease.

Figure 8:
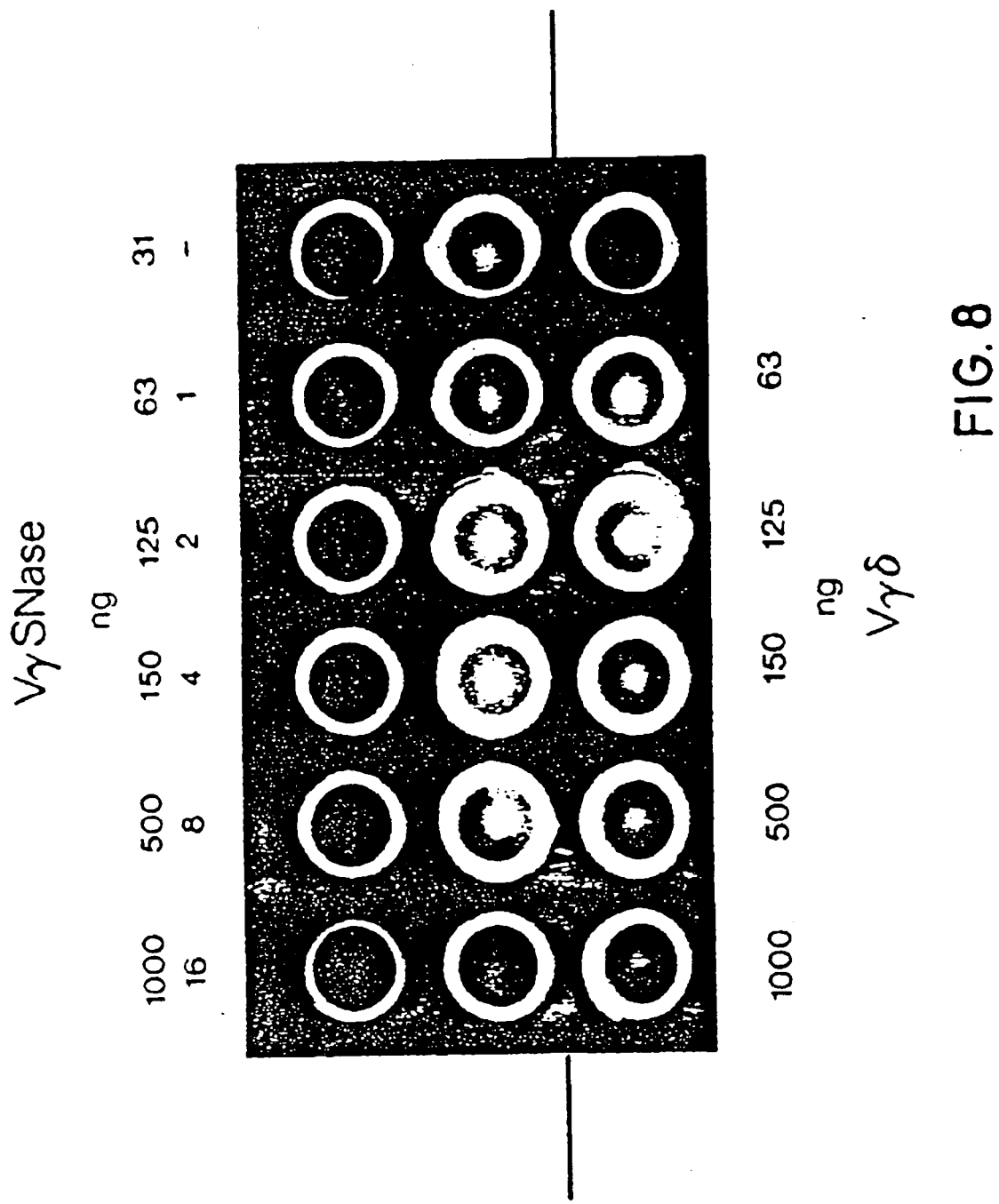
FIG. 8 shows an EISA-type assay.

The V$_{NP}$ γ SNase chimeric antibody can be used as a genetically conjugated enzyme linked antibody in ELISA-type assays as shown in FIG. 8. Antigen coated plastic plates were incubated with various amounts of V$_{NP}$ γ SNase protein and bound antibody was then detected by virtue of its nuclease activity. This was achieved by addition to the plate of a solution containing DNA and ethidium bromide. Following digestion of the DNA substrate by the immobilized V$_{NP}$ γ SNase antibody, the fluorescence due to the DNA/ethidium bromide complex substantially decreased.

In particular, polyvinyl nicrotitre plates were coated with (NIP)$_{20}$—bovine serum albumin (40 μg ml). After blocking unreacted sites with BSA, dilutions of V$_{NP}$ γ SNase or V$_{NP}$ γδ chimeric antibodies were incubated in the wells, the amounts of antibody being given in nanograms in FIG. 8. After washing off unbound material, a solution (40 μl) containing 1 μg M13 single stranded DNA and 1 ug/ml ethidium bromide in pH 8.5 buffer was added. The plate was photographed after a 1 hour incubation at 37° C.

As shown in FIG. 8, quantities in the range of 10 ng of V$_{NP}$ γ SNase antibody are easily detected and no decrease in fluorescence is obtained with the V$_{NP}$ γδ antibody control. We have found that the assay may be made at least tenfold more sensitive by increasing the incubation time with the DNA substrate.

EXAMPLE 3

Fab-myc Chimeric Antibody

The carboxyterminal portion of the souse c-myc gene was fused to the antibody Fab. The product of the c-myc gene is a protein which contains many thiol groups and is normally resident within the cell. There is no reason to believe that the third exon of c-myc on its own will encode a functional protein domain. Thus, if the Fab-myc fusion protein were secreted from the cell it would provide a source of protein for making anti-myc antisera.

Plasaid pSV-V$_{NP}$ γ myc was assembled essentially as described for the assembly of pSV-V$_{NP}$ γδ except that the pSV-V$_{NP}$ γδ Sac I-Xho I fragment containing the Cδ$_s$ exon was replaced by a Sac I-Bgl II fragment containing the 3' exon of mouse c-myc. The restriction site in FIG. 9 marked Bg/B is a site formed by joining the Bgl II site at the 3' end of c-myc to the Bam HI site of pSV2gpt. The c-myc fragment comes from phage λ MYG2, which contains the translocated c-myc gene of mouse plasmacytoma X63Ag8 (see Neuberger and Calabi, loc. cit).

The plasmid is similar in structure to pSV-V$_{NP}$ γδ except that the Cδ$_s$ exon is replaced with the 3'-terminal exon of the mouse c-myc gene. This c-myc exon encodes 187 aminoacids (see Bernard, O., Cory, S., Gerondatis, S., Webb, E. and Adams, J. M., EHBO J., 2375–2383, 1983) and should provide the transcription polyadenylation signal.

The plasmid was transfected into J558L and cells trom wells positive for production of anti-NP antibody cloned by limiting dilution. Hapten-binding protein was purified from culture supernatants and analyzed for the presence of c-myc antigenic determinants in an indirect radioimmunoassay.

Samples of either the putative Fab-myc or of the anti-NP F(ab)'$_2$ (to act as control) were incubated in wells of a polyvinyl microtitre plate that had been coated with a monoclonal anti-c-myc antibody; bound anti-NP antibody was then detected using a radiolodinated monoclonal anti-idiotope antibody which recognises the Fab portion of the anti-NP antibodies.

As shown in FIG. 10, the Fab-myc clearly binds to the monoclonal anti-c-myc antibody, whereas the anti-NP F(ab)'2 and other controls do not. The Fab-myc was also recognized by two other sonoclonal antibodies that are specific for the carboxyteminal end of c-myc. SDS/polyacrylamide gel electrophoresis of the Fab-myc reveals that it is somewhat heterogenous; a band comigrating with $\lambda_1$ light chains and several bands with higher molecular weight in the range 38,000 to 55,000 daltons are observed, without a single dominant heavy chain band being apparent. The expected size of the Fab-myc is 50,000 daltons. It has been observed that, after prolonged storage, precipitates appear in the Fab-myc sample and SDS/polyacrylamide gel electrophoresis reveals more extensive heterogeneity of the heavy chain bands. We therefore believe that the heterogeneity of the Fab-myc protein indicated by the SDS/polyarcylamide gel analysis is most probably due to proteolytic degradation.

EXAMPLE 4

Chimeric Mouse—Human Antibodies

A plasmid pSV-V$_{NP}$H $\epsilon$ was constructed as follows. The Eco RI-Bam HI fragment of plasmid pSV-V$\mu$l was cloned between the Eco RI and Bam HI sites of plasmid pSV2gpt to yield pSV-V$_{NP}$. The Bam HI fragment of phage $\lambda\epsilon$1.2 (see Flanagan J. G. and Rabbitts, T. H., EMBO J., 1, 655–660, 1982), which includes exons C$\epsilon$1 to C$\epsilon$4 of the human $\epsilon$ gene was cloned into pSV-V$_{NP}$ and the plasmid pSV-V$_{NP}$H$\epsilon$ completed by including in its unique Eco RI site the Xba I-Eco RI enhancer-containing fragment of the mouse heavy chain locus.

The structure of the pSV-V$_{NP}$H$\epsilon$ plasld is shown in FIG. 11 and encodes for a heavy chain comprising a mouse variable region and a human $\epsilon$ constant region.

pSV-V$_{NP}$H$\epsilon$ was introduced into J558 ceils by spheroplast fusion, and stably transfected clones were selected as described above. Transfectants were obtained with a frequency of between $10^{-3}$ and $10^{-4}$. Culture supernatants were assayed for production of $\lambda$1—bearing anti-NP antibodies by radiolmmunoassay as described above. Between 50 and 80% of the clones were positive. Antibody was purified from culture supernatants of several transfected clones by affinity chromatography as described above, with yield of about 2 mg per liter.

Figure 12:
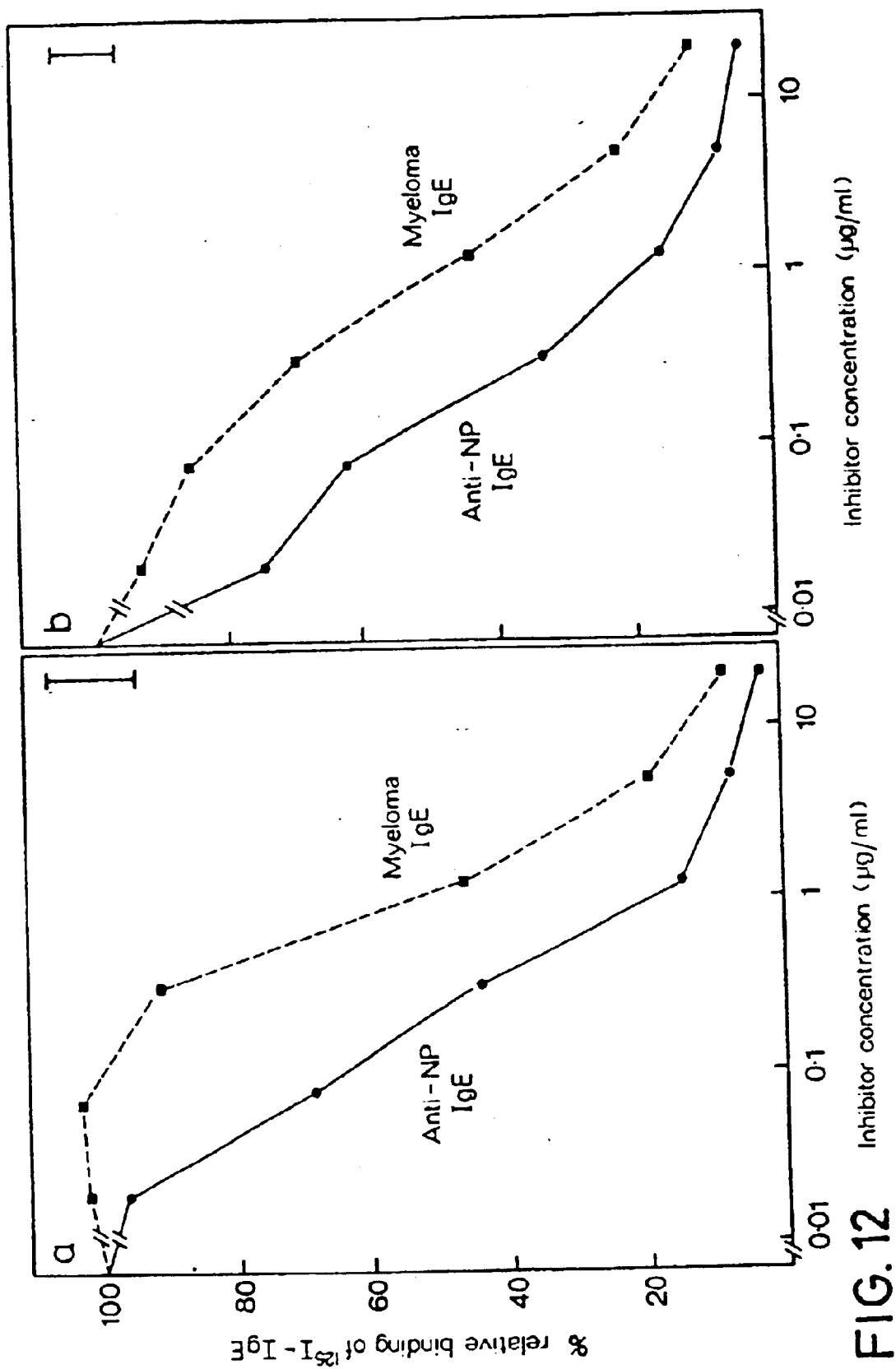
FIG. 12 shows a serological analysis of chimeric IgE by binding inhibition assays.

Binding inhibition assays were used to demonstrate that the purified chimeric antibody displayed human antigenic determinants (FIG. 12).

Assays were performed in which the binding of a radio-iodinated human myeloma IgE to either a monoclonal (a) or polyclonal (b) anti-human $\epsilon$ antiserum was inhibited by various concentrations of unlabelled chimeric IgE (●) of unlabelled myeloma IgE (■).

Wells of a Dynatec microtitre plate were coated with a solution containing either 1 $\mu$g.ml$^{-1}$ of a monoclonal mouse anti-human $\epsilon$ antibody (antibody RB6-2; given by M. D. Cooper) or 3 $\mu$g ml$^{-1}$ of a polyclonal sheep anti-human $\epsilon$ antiserum (Seward Laboratory). After blocking of unreacted sites with bovine serum albumin, a human myeloma IgE (Serotec) that had been radiolabelled with $^{125}$I was incubated in the wells in the presence of different concentrations of either chimeric IgE or unlabelled myeloma IgE itself.

The affinity-purified chimeric antibody competes with the binding of radiolabelled human myelona IgE to both monoclonal (FIG. 12A) and polyspecific (FIG. 12B) anti-$\epsilon$antisera. Furthermore, binding of radiolabelled myeloma IgF to the anti-$\epsilon$ antiserum was inhibited completely (FIG. 12B), indicating that the chimeric antibody displays all the $\epsilon$ antigenic determinants recognised by this polyclonal antiserum. The chimeric antibody competed with the binding of the radiolabelled myeloma IgE to the anti-$\epsilon$ antisera better than did the unlabelled myeloma IgE itself, probably because the purified chimeric antibody is essentially homogenous (see FIG. 13), whereas the commercial sample of myeloma IgE is not.

The structure of the chimeric protein vas investigated by SDS-polyacrylamide gel electrophoresis (SDS-PAGE). Examination of reduced anti-NP IgE reveals a band comigrating with mouse $\lambda$1 light chains and a diffuse heavy-chain band of relative molecular mass (M$_r$)~72,000 (72K) (FIG. 13A); this is considerably larger than the M$_r$ of the $\epsilon$ polypeptide chain as predicted from the DNA sequence. However, this discrepancy is resolved by SDS-PAGE of biosynthetically labelled anti-NP IgE secreted by cells labelled in the presence of tunicamycin (FIG. 13B). Incubation with this glycosylation inhibitor reduces the apparent relative molecular mass of the secreted anti-NP IgE from 72K to the predicted value of 62K. Thus, the chimeric IgE, like IgE from human myeloma, is heavily glycosylated. The electrophoretic mobility of unreduced anti-NP IgE in SDS polyacrylamide gels is consistent with it having an $\epsilon_2\lambda_2$ structure.

FIG. 13A shows the SDS-PAGE results obtained from purified antibody (30 $\mu$g) from a cloned pSV-V$_{NP}$H$\epsilon$ transfectant of J558L (JW8/5/13) which was boiled in the presence of 2-mecaptoethanol, subjected to electraphoresis through a 9% gel and stained with Coomassie blue. In FIG. 13B, the results are shown for biosynthetically labelled antibody from either J558L or the transfectant JW8/5/13 which was purified on NIP-Sepharose columns and analysed on a 7% gel after reduction. Samples purified from cells labelled in the presence of tunicamycin are marked +Tm. The positions of relative molecular mass markers are indicated (94K=relative molecular mass 94,000). Biosynthetic labelling with [L-$^{35}$S] methionine and purification of both labelled and unlabelled samples on hapten-Sepharose columns were performed as described above.

Two types of assay were performed to determine whether the chimeric anti-NP IgE antibody exhibits the physiological effector functions of authentic human IgE. In one type of assay, the ability of the antibody to trigger histamine release from human basophils was tested. A preparation of mononuclear cells from peripheral blood containing 1–2% basophils was passively sensitized with the chimeric antibody before incubation with hapten (5-iodo-4-hydroxy-3-nitrophenacetyl caproate, NIP) coupled to bovine serum albumin (NIP-BSA). The results (Table 1) Indicate that, after preincubation of basophils with the chimeric IgE, NIP-BSA is able to trigger a dose-dependent release of histamine. A heterologous antigen, antigen P1 of the house dust mite *Dermatophagoides pteronyssinus*, failed to induce histamine release. Similarly, only background levels of histamine release were obtained with either the chimeric antibody or NIP-BSA alone. These results indicate that the anti-NP IgE, like authentic human IgE, will not cause degranulation by itself, but will trigger histamine release following crosslinking with antigen.

In a second assay, it was demonstrated that incubation with anti-NP IgE could also block the subsequent passive sensitization of basophils by atopic sera containing high IgE levels. Table 2 shows that house dust site antigen P1 can induce the release of histamine from basophile preincubated with serum containing anti-PI IgE antibody. However, this same serum failed to effect histamine release when the cells had been incubated previously with the chimeric antibody at concentrations >0.1 $\mu$g ml$^{-1}$.

The results described her demonstrate that transfection of DNA into mouse myeloma cells is an effective way of producing large amounts of chimeric antibodies in which mouse V regions provide antigen-binding specificity and human $C_H$ regions provide human effector functions. The known antigenbinding specificty of such an antibody makes its purification extremely simple. Production of a chimeric IgE in this vay has proved particularly attractive as no monoclonal human IgE of known antigen specificity was previously available. The chimeric antibody may, therefore, prove useful in routine clinical assays. It has been demonstrated that this monoclonal IgE is able to block the release of histamine from human basophils which can be triggered in vitro by sera from allergic subjects. It will clearly be important to discover whether analogous blocking can be achieved in vivo using skin sensitization assays.

TABLE 1

Histamine release triggered from human basophils passively sensitized with chimeric IgE

| Antigen | % Histamine release (±s.e.m.) |
|---|---|
| — | 6.4 + 0.8 |
| 10 $\mu$g ml$^{-1}$ NIP-BSA | 18.4 + 2.4 |
| 1 $\mu$g ml$^{-1}$ NIP-BSA | 36.0 + 5.6 |
| 0.1 $\mu$g ml$^{-1}$ NIP-BSA | 31.2 + 12.0 |
| 0.01 $\mu$g ml$^{-1}$ NIP-BSA | 26.4 + 2.4 |
| 0.001 $\mu$g ml$^{-1}$ NIP-BSA | 7.2 + 1.6 |
| 0.0001 $\mu$g ml$^{-1}$ NIP-BSA | 5.2 + 1.2 |
| 20 $\mu$g ml$^{-1}$ Antigen P1 | 4.5 + 0* |

Mononuclear cells were prepared from peripheral blood by sedimentation through dextran-EDTA; these preparations contained 1–2% basophils. Cells were incubated in duplicate at 37° C. for 2 h in complete Tyrode's buffer with 1.5 $\mu$g ml$^{-1}$ chimeric anti-NP IgE. Cells were then centrifuged and resuspended in complete Tyrode's buffer containing the indicated concentrations of (NIP)$_{30}$-BSA. After 15 min, the histamine released into the supernatant was extracted and assayed fluorimetrically. The maximum histamine release that could be obtained by incubating the cells at 100° C. was 62.5 ng ml$^{-1}$. The results are expressed as percentage histamine release; (antigen-induced histamine release [ng ml$^{-1}$])×100/maximum histamine release obtainable (ng ml$^{-1}$). The mean background percentage release obtained in repeated experiments was 6.0±2.5. Both NIP-BSA (1.0 $\mu$q ml$^{-1}$) and antigen P1 (20 $\mu$g ml$^{-1}$) alone repeatedly failed to induce histamine release above background levels.

*Data obtained in a separate experiment using cells from the same donor.

TABLE 2

Blocking of histamine release by preincubation with chimeric IgE

| Concentration ($\mu$g ml$^{-1}$) of chimeric anti-NP IgE in preincubation | Serum from allergic subject | Antigen P1 | % Histamine release (±s.e.m.) |
|---|---|---|---|
| — | + | + | 20.5 + 2.7 |
| 0.01 | + | + | 16.9 + 2.4 |
| 0.1 | + | + | 7.2 + 0 |
| 1 | + | + | 8.2 + 1.0 |
| 10 | + | + | 7.2 + 1.0 |
| 10 | − | − | 8.4 + 1.2 |
| − | − | + | 7.5 + 1.7 |

Mononuclear cells were prepared as described in Table 1. A 2-h incubation with different concentrations of chmeric anti-NP IgE was followed by a 2-h incubation with allergic serum (diluted 1:30 in complete Tyrode's), prior to a 15-min exposure to antigen P1 (20 $\mu$g ml$^{-1}$). The allergic serum used had a total IgE level of 4,800IU ml$^{-1}$, and 1,600 BA units ml$^{-1}$ of IgE specific for *D. pteronyssinus* antigen P1. The maximum histamine release by incubating the cells used in this experiment at 100° C. was 10.4 ng ml$^{-1}$.

EXAMPLE 5

Fab-γ-Klenow Chimeric Antibody

A plasmide pSV-V$_{NP}$ γ Klenow, which encodes the heavy chain of a recombinant antibody in which the Klenow fragment of DNA polymerase I is fused to the Fab portion of a mouse IgG2b molecule, was assembled.

The construction of pSV-V$_{NP}$ γ Klenow is analogous to that previously described for pSV-V$_{NP}$ γ SNase. The coding region for the Klenow fragment of DNA polymerase I was obtained as a BamHI fragment by combining two plasmids, pCJ14 (C. M. Joyce and N. G. D. Grindley, PNAS USA. 80, 130–1834, 1983) and pCJ89 (C. M. Joyce and N. G. D. Grindley, *J. Bacteriol.*, 158, 636–643, 1984), in which BamHI linkers have been inserted on either side of the Klenow coding region. This BamHI fragment was converted into a Sal I fragment by use of linkers and inserted into the unique Xho I site of pSV-V$_{NP}$ γ2b (CH2, CH3).

This antibody/enzyme fusion gene contains a variable region, V$_{NP}$, such that association of the pSV-V$_{NP}$ γ Xlenow heavy chain with the mouse immunoglobulin λ light chain from the J558L cell line will form a binding site for the bapten 4-hydroxy-3-nitrophenacetyl (NP). The V$_{NP}$ gene is linked to exons encoding the CB1, hinge and aminoterminal part of the CH2 domain of a mouse immunoglobulin γ2b heavy chain. The DNA encoding the rest of CH2 and all of CH3 has been replaced by a fragment of the *E. coli* DNA polymerase I gene that specifies the 5'-3' polymerase and 3'-5' exonuclease activities (the Klenow fragment). This Fab-Klenow fusion gene was cloned into the plasmid vector pSV2gpt which provides a polyadenylation signal for the Fab-Klenow transcription unit and also provides a marker, gpt, that confers resistance to the drug mycophenolic acid and thus allows selection of stably transfected mammalian cells.

Spheroplast fusion was used as a means to introduce pSV-V$_{NP}$ γ Klenow DNA into J558L cells. (The procedure used for protoplast fusion and selection of transfected clones is described in detall by M. S. Neuberger and G. T. Williams in *Protein engineering: applications in science, medicine and industry* (M. Inouye and R. Sarma, eds.), Academic Press,) Stable transfectants were selected in medium containing mycophenolic acid and the presence of NP-specific antibody in the culture medium of such transfectanta was identified by radloimmunoassay. The transfectants were cloned by limitiug dilution and one particular clone, JW64/7, that gave a high antibody titre was chosen for further study.

Figure 15:
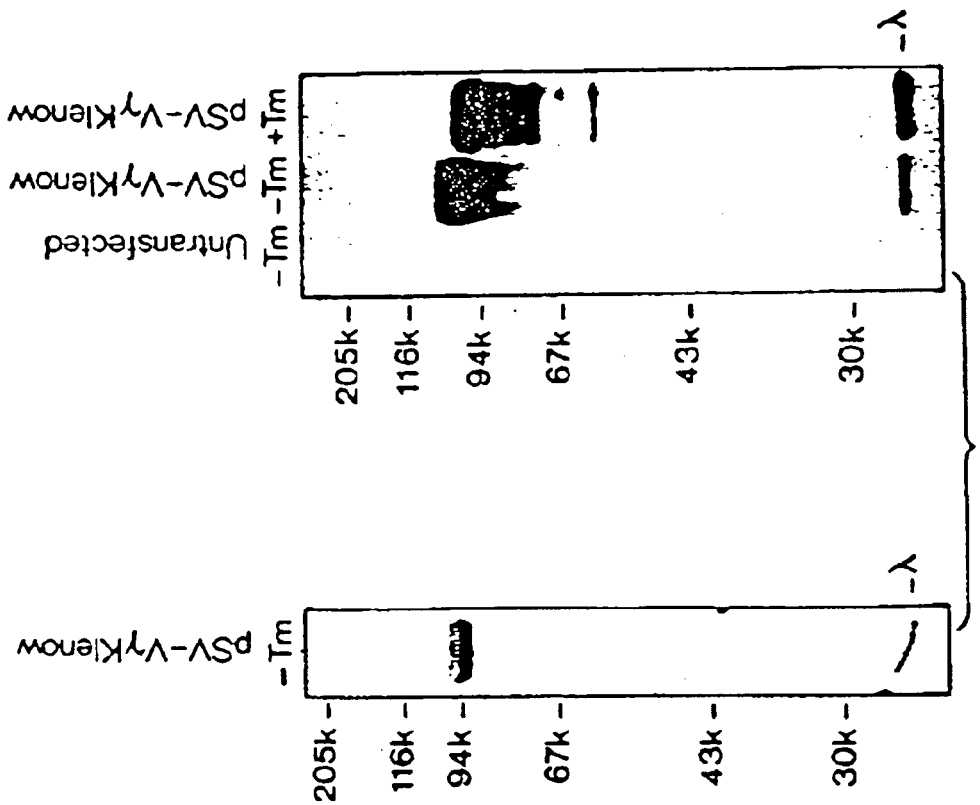
FIG. 15 shows polyacrylamide gels of the purified Fab-γ Klenow chimeric antibody.

The protein secreted by JW64/7 was examined by SDS/polacrylamide gel electrophoresis of biosynthetically labelled samples that had been purified on hapten-Sepharose sorbeant (FIG. 15B). As expected from the predicted structure of the Fab-Klenow protein (FIG. 14B), the gel reveals the presence of two polypeptide chains: a band corresponding to $\lambda_1$ light chain and a heavy chain of mol. wt. about 96,000 (FIG. 15B). Within the Klenow portion of the Fab-Klenow heavy chain, four sequences of the form Asn-X-Thr/Ser are encountered; these might constitute sites for N-linked glycosylation. In order to discover whether the Fab-Klenow heavy chain is in fact glycosylated, biosynthetic labelling experiments were performed in the presence of the glycosylation inhibitor tunicamycin. The results (FIG. 15B) reveal that tunicamycin does indeed result in the synthesis of a heavy chain of reduced molecular weight.

Fab-Klenow protein was purified by affinity chromatography on NP-Sepharose from culture supernatant of JW64/7 grown in DMEM/10% foetal calf serum, giving a homogeneous preparation (FIG. 15A). The yield varied in the range of 1 to 15 mg of protein per liter of culture supernatant. The 5'-3' polymerase activity of the purified protein was measured using the classical assay (The assay was performed as described by P. Setlow, *Methods Enzymol.* 29, 3–12, 1974.) in which the enzyme is incubated with "actlvated" DNA and the four dNTPs, one of which is radiolabelled; the incorporation of radioactivity into acid-precipitable material is followed. In this assay, using activated calf thymus DNA as substrate, the Fab-Klenow gave an activity of about $1.1 \times 10^3$ units/mg as compared to a value of $7 \times 10^3$ units/mg obtained under the same assay conditions using a commercial sample of homogeneous Klenow fragment which had been prepared by proteolytic fragmentation of DNA polymerase I purified from *E. coli*. A decreased specific activity (expressed as units per ag protein) of the Fab-Klenow compared to the normal enzyme is to be expected in view of their different molecular weights. Hovever, this can only account for part of the difference in activity. Examination of unreduced Fab-Klenow in SDS/polacrylamide gels (not shown) suggests the presence of divalent $F(ab')_2$-Klenow as well as monovalent protein. It is possible that the $F(ab')_2$-Klenow might only show half-site reactivity; alternatively, it might be that glycosylation reduces the specific activity of the Fab-Klenow.

Figure 16:
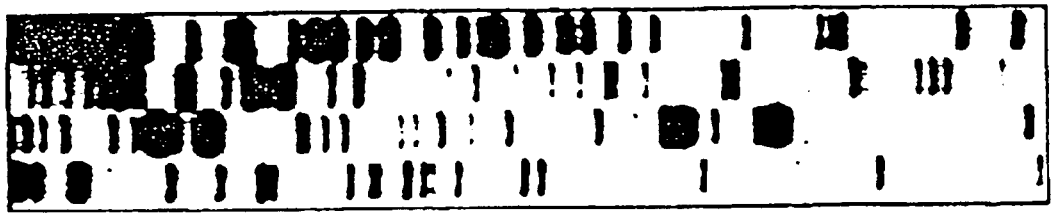
FIG. 16 shows an assay for Klenow fragment activity.

A major use of DNA polymerase I Klenow fragment is in the chain termination of DNA sequencing. As shown in FIG. 16, Fab-Klenow can indeed be used successfully for this purpose. FIG. 16 shows the use of Fab-Klenow in chain termination DNA sequencing. DNA from an M13 clone was sequenced using Fab-Klenow as described by Sanger et al. (F. Sanger, S. Nicklen and A. R. Coulson, PNAS USA, 74, 5463–5476, 1077) using 1 unit per clone of Fab-Klenow.

Thus it has been shown that recombinant antibody technology can usefully be applied to the tagging of specific enzymes such that they are secreted from the cell and can be readily purified to homogeneity in a one step purification.

Conclusion

The above Examples demonstrate that by using the process of the present invention, it is possible to produce secreted, functional chimeric antibodies, which was not previously possible. The process enables the production of a number of chimeric antibodies which have not previously been know.

What is claimed is:

1. A chimeric antibody comprising an Ig moiety having antigen binding activity and a non-Ig protein moiety comprising a protein having biological activity or a biologically active portion thereof, wherein said non-Ig protein moiety is attached by peptide linkage to said Ig moiety and is carboxy terminal to said Ig moiety, said chimeric antibody having said antigen binding activity and said biological activity.

2. The chimeric antibody of claim 1 wherein said non-Ig protein is selected from the group consisting of enzymes, toxins, and proteins with known binding specificity.

3. The chimeric antibody of claim 2 wherein said enzyme is the Klenow fragment of DNA polymerase I.

4. The chimeric antibody of claim 2 wherein said toxin is ricin.

5. The chimeric antibody of claim 2 wherein said protein of known binding specificity is c-myc.

6. A process for the production of a chimeric antibody comprising an Ig moiety having antigen binding activity and an non-Ig protein moiety comprising a protein having biological activity or a biologically active portion thereof, wherein said non-Ig protein moiety is carboxy terminal to said Ig moiety, said chimeric antibody having said antigen binding activity and said biological activity, said process comprising;

i) preparing a replicable expression vector comprising a promoter operably linked to a DNA sequence comprising a first part encoding at least a variable region of an antigen-binding Ig polypeptide chain and a second part 3' of said first part encoding a biologically functional non-Ig protein, or a biologically active portion thereof, wherein said first and second parts are combined such that expression results in a product possessing said variable region capable of binding antigen and said non-Ig protein capable of exhibiting its biological function as expressed;

ii) transforming an immortalized mammalian cell line that secretes an Ig polypeptide chain complementary to the variable region encoded in said DNA sequence with said vector, and iii) culturing the transformed cell line under conditions such that said DNA sequence is expressed and such that assembly of said chimeric antibody is effected so that said variable region is immunologically active and said non-Ig protein moiety is biologically functional.

7. The method of claim 6 wherein the immortalized cell line is of myeloid origin.

8. The method of claim 6 wherein the immortalized cell line is a myeloma, hybridoma, trioma, or quadroma cell line or an immortalised B-cell.

9. A process for the production of a chimeric antibody comprising an Ig moiety having antigen binding activity and a non-Ig protein moiety comprising a protein having biological activity or a biologically active portion thereof, wherein said non-Ig protein moiety is carboxy terminal to said Ig moiety, said chimeric antibody having said antigen binding activity and said biological activity, said process comprising:

i) preparing a first replicable expression vector comprising a promoter operably linked to a DNA sequence comprising a first part encoding at least a variable region of an antigen-binding Ig polypeptide chain and a second part 3' of said first part encoding a biologically functional non-Ig protein, or a biologically active portion thereof, wherein said first and second parts are combined such that expression results in a product possessing said variable region capable of binding antigen and said non-Ig protein capable of exhibiting its biological ftmction as expressed;

ii) preparing a second replicable expression vector comprising a promoter operably linked to a DNA sequence encoding at least a variable region of an Ig polypeptide chain complementary to said variable region encoded in said DNA sequence of step (i);

iii) transforming an immortalized mammalian cell line with said first and second expression vectors prepared in steps and (ii); and iv) culturing the transformed cell line resulting from step (iii) under conditions such that said DNA sequences are expressed and that assembly of said chimeric antibody is effected so that said variable region is immunologically active and said non-Ig protein moiety is biologically functional.

10. The method of claim 9 wherein the immortalized cell line is of myeloid origin.

11. The method of claim 9 wherein the immortalized cell line is a myeloma, hybridoma, trioma or quadroma cell line or an immortalised B-cell.

* * * * *